US00PP15858P2

(12) United States Plant Patent
Dümmen

(10) Patent No.: US PP15,858 P2
(45) Date of Patent: Jul. 12, 2005

(54) ***GERANIUM* PLANT NAMED 'DUEAZULIA'**

(50) Latin Name: *Pelargonium×hortorum*
Varietal Denomination: Dueazulia

(75) Inventor: Marga Dümmen, Rheinberg (DE)

(73) Assignee: Dümmen Jungpflazen GbR, Rheinberg (DE)

( * ) Notice: Subject to any disclaimer, the term of this patent is extended or adjusted under 35 U.S.C. 154(b) by 0 days.

(21) Appl. No.: 10/859,499

(22) Filed: Jun. 1, 2004

(51) Int. Cl.[7] ..... A01H 5/00
(52) U.S. Cl. ..... Plt./329
(58) Field of Search ..... Plt./329

(56) References Cited

U.S. PATENT DOCUMENTS

PP9,206 P * 7/1995 Klemm ..... Plt./329
PP11,440 P * 7/2000 Trees ..... Plt./329
PP11,676 P * 12/2000 Trees ..... Plt./329
PP13,201 P2 * 11/2002 Dummen ..... Plt./329

OTHER PUBLICATIONS

UPOV ROM GTITM Computer Database, GTI Jouve Retrieval Software 2004/04 Citation for 'Dueazulia'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of Zonal *Geranium* plant named 'Dueazulia', characterized by its upright, somewhat outwardly spreading and rounded plant habit; freely branching habit; dark green-colored foliage; freely and early flowering habit; and red purple-colored semi-double flowers.

1 Drawing Sheet

Botanical designation: *Pelargonium×hortorum.*
Variety denomination: 'Dueazulia'.

BACKGROUND OF THE INVENTION

The present invention relates to a new and distinct cultivar of Zonal *Geranium* plant, botanically known as *Pelargonium×hortorum,* and hereinafter referred to by the name 'Dueazulia'.

The new Zonal *Geranium* is a product of a planned breeding program conducted by the Inventor in Rheinberg, Germany. The objective of the breeding program was to develop new freely and early flowering Zonal *Geraniums* with attractive flower and foliage colors.

The new Zonal *Geranium* originated from a cross-pollination made by the Inventor in May, 1998, of two unnamed selections of *Pelargonium×hortorum,* not patented. The cultivar Dueazulia was discovered and selected by the Inventor as a single flowering plant within the progeny from this stated cross-pollination in a controlled environment in Rheinberg, Germany in April, 2001.

Asexual reproduction of the new cultivar by terminal vegetative cuttings at Rheinberg, Germany since July, 2001, has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Dueazulia'. These characteristics in combination distinguish 'Dueazulia' as a new cultivar and distinguish it from other known Zonal *Geranium* cultivars:

1. Upright, somewhat outwardly spreading and rounded plant habit.
2. Freely branching habit.
3. Dark green-colored foliage.
4. Freely and early flowering habit.
5. Red purple-colored semi-double flowers.

Plants of the new Zonal *Geranium* differ from plants of the parent selections in flower color.

The new Zonal *Geranium* can be compared to plants of the cultivar Arcona 2000, not patented. In side-by-side comparisons conducted in Rheinberg, Germany, plants of the new Zonal *Geranium* differed from plants of the cultivar Arcona 2000 in the following characteristics:

1. Plants of the new Zonal *Geranium* were more densely foliated than plants of the cultivar Arcona 2000.
2. Flowers of plants of the new Zonal *Geranium* were more red purple in color than flowers of plants of cultivar Arcona 2000.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of a typical flowering plant of 'Dueazulia' grown in a container.

DETAILED BOTANICAL DESCRIPTION

The cultivar Dueazulia has not been observed under all possible environmental conditions. The phenotype may vary somewhat with variations in environment, such as temperature and light intensity, without, however, any variance in genotype.

The aforementioned photograph, following observations and measurements describe plants grown in Rheinberg, Germany during the summer under commercial practice in a glass-covered greenhouse with day and night temperatures about 18° C. and light levels about 4,500 foot-candles. Plants were grown in 10.5-cm containers. Plants were pinched once about three weeks after planting. Plants were about eight weeks from unrooted cuttings when the photograph and the detailed botanical description were taken.

In the following description, color references are made to The Royal Horticultural Society Colour Chart, 1995 edition, except where general terms of ordinary dictionary significance are used.

Botanical classification: *Pelargonium×hortorum* cultivar Dueazulia.

Parentage:

*Female parent.*—Unnamed selection of *Pelargonium× hortorum,* not patented.

*Male parent.*—Unnamed selection of *Pelargonium× hortorum,* not patented.

Propagation:

*Type cutting.*—Terminal vegetative cuttings.

*Time to initiate roots.*—Summer: About 5 days at 20° C. Winter: About 7 days at 20° C.

*Time to develop roots.*—Summer: About three weeks at 20° C. Winter: About four weeks at 20° C.

*Root description.*—Fine, fibrous; white in color.

*Rooting habit.*—Freely branching.

Plant description:

*General appearance.*—Upright, somewhat outwardly spreading and rounded plant habit; densely foliated.

*Growth and branching habit.*—Moderately vigorous. Freely branching, about eight lateral branches per plant.

*Plant height.*—About 35 cm.

*Plant width.*—About 21 cm.

*Lateral branches.*—Length: About 28.6 cm. Internode length: About 3.2 cm. Texture: Smooth. Color: 144A.

*Foliage description.*—Arrangement: Alternate, single. Length: About 6.1 cm. Width: About 9.4 cm. Shape: Reniform. Apex: Rounded. Base: Cordate. Margin: Crenate. Venation pattern: Palmate. Texture, upper and lower surfaces: Pubescent. Color: Developing and fully expanded foliage, upper surface: 137A, no zone coloration displayed to date. Developing and fully expanded foliage, lower surface: 137C. Venation, upper and lower surfaces: 144A. Petiole: Length: About 7.5 cm. Diameter: About 2.7 mm. Color, upper and lower surfaces: 144A.

Flower description:

*Flower arrangement.*—Bright red purple-colored semi-double flowers arranged in rounded hemispherical umbels arising from apical leaf axils. Umbels displayed above and beyond the foliage on peduncles. Flowers rounded in form. Umbels persistent, flowers not persistent. Flowers not fragrant.

*Quantity of flowers.*—Freely flowering; at full flower, plants have about eleven open umbels with about 23 flowers per umbel.

*Flowering season.*—Flowering continuous spring until the autumn. Plants begin flowering about six weeks after planting.

*Flower longevity.*—Flowers last about five to seven days on the plant.

*Umbel size.*—Diameter: About 9.2 cm. Height: About 6.6 cm.

*Flower size.*—Diameter: About 3.6 cm. Depth (height): About 2 cm.

*Flower buds.*—Length: About 10.3 mm. Diameter: About 7.5 mm. Shape: Ovoid. Color: 144A.

*Petals.*—Quantity per flower: About five or six. Length: About 2.2 cm. Width: About 2.1 cm. Shape: Obovate. Apex: Rounded. Base: Attenuate. Margin: Entire; sinuate. Texture, upper and lower surfaces: Smooth. Color: When opening and fully opened, upper surface: 74A; towards the base, 50A. When opening and fully opened, lower surface: 74A; towards the base, 50A.

*Petaloids.*—Quantity per flower: About two to four. Length: About 2.2 cm. Width: About 1.1 cm. Shape: Obovate. Apex: Rounded. Base: Attenuate. Margin: Entire; sinuate. Texture, upper and lower surfaces: Smooth. Color: When opening and fully opened, upper surface: 74A; towards the base, 50A. When opening and fully opened, lower surface: 74A; towards the base, 50A.

*Sepals.*—Quantity per flower: About five or six, arranged in a single whorl. Length: About 1.2 cm. Width: About 3.2 mm. Shape: Elongated, tapering. Apex: Apiculate. Margin: Entire. Texture, upper and lower surfaces: Smooth, glabrous. Color, upper and lower surfaces: 144A.

*Peduncle* (*umbel stem*).—Length: About 17.5 cm Diameter: About 2 cm. Angle: Mostly erect. Strength: Moderately strong. Texture: Smooth; glabrous. Color: 144A.

*Pedicel* (*individual flower stem*).—Length: About 2.9 cm. Diameter: About 7.5 mm. Angle: Mostly erect. Strength: Moderately strong. Texture: Pubescent. Color: 59B.

*Reproductive organs.*—Androecium: Anther quantity per flower: About five to ten. Anther length: About 3 mm. Anther shape: Ovate. Anther color: 41A to 41C. Pollen amount: Moderate. Pollen color: 28A. Gynoecium: Pistil quantity per flower: One. Pistil length: About 7.5 mm. Stigma shape: Five-parted, star-shaped. Stigma color: 60A to 60B. Style length: About 2.3 mm. Style color: 144C. Ovary color: 144A.

*Seed/fruit.*—Development of seeds and fruit have not been observed.

Disease/pest resistance: Plants of the new Zonal *Geranium* have not been observed to be resistant to pathogens and pests common to Zonal *Geraniums.*

Temperature tolerance: Plants of the new Zonal *Geranium* have been observed to be tolerant to temperatures ranging from 5 to 40° C.

It is claimed:

1. A new and distinct cultivar of Zonal *Geranium* plant named 'Dueazulia', as herein illustrated and described.

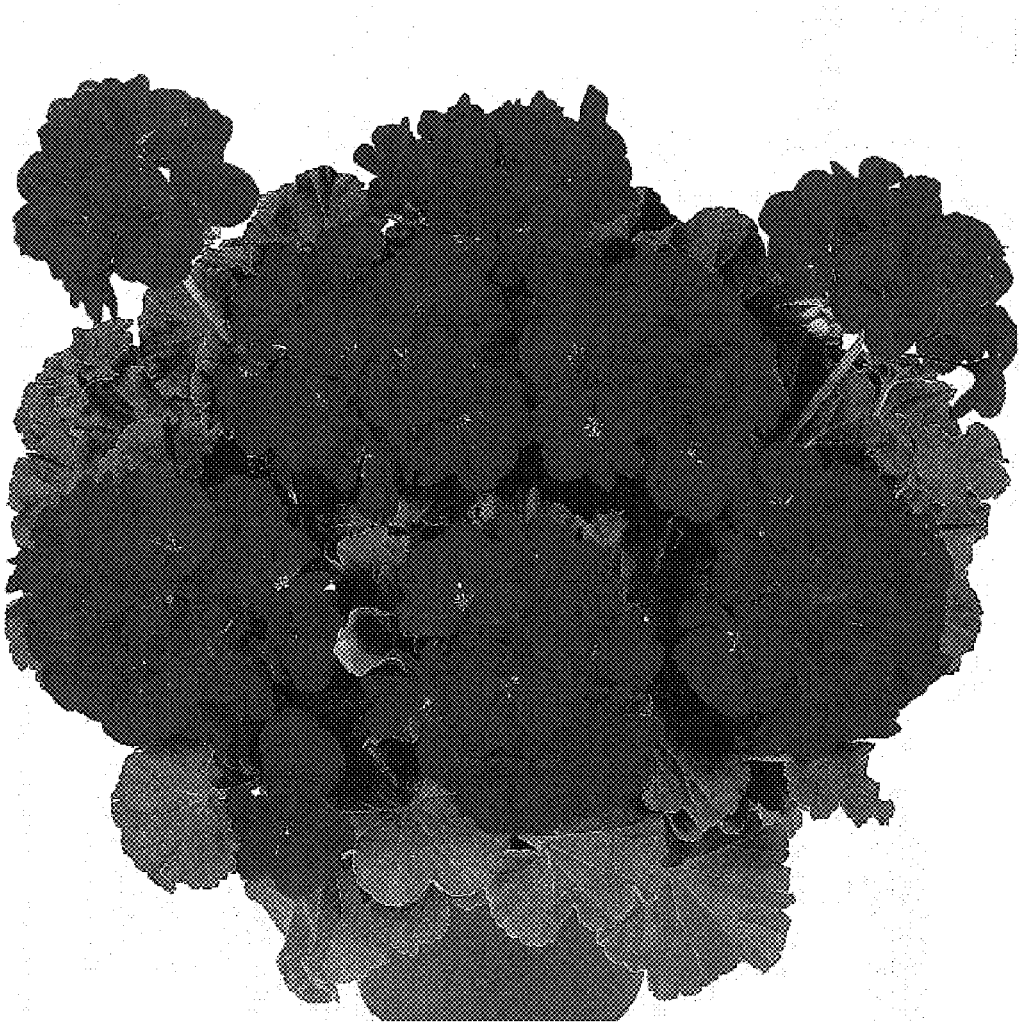

* * * * *